United States Patent
Weingarten et al.

(10) Patent No.: US 11,864,935 B2
(45) Date of Patent: Jan. 9, 2024

(54) SYSTEMS AND METHODS FOR POSE ESTIMATION OF A FLUOROSCOPIC IMAGING DEVICE AND FOR THREE-DIMENSIONAL IMAGING OF BODY STRUCTURES

(71) Applicant: COVIDIEN LP, Mansfield, MA (US)

(72) Inventors: Oren P. Weingarten, Herzliya (IL); Guy Alexandroni, Herzliya (IL); Evgeni Kopel, Herzliya (IL)

(73) Assignee: Covidien LP, Mansfield, MA (US)

( * ) Notice: Subject to any disclaimer, the term of this patent is extended or adjusted under 35 U.S.C. 154(b) by 111 days.

(21) Appl. No.: 16/924,776

(22) Filed: Jul. 9, 2020

(65) Prior Publication Data
US 2021/0068772 A1 Mar. 11, 2021

Related U.S. Application Data

(60) Provisional application No. 62/897,760, filed on Sep. 9, 2019.

(51) Int. Cl.
*A61B 6/12* (2006.01)
*A61B 34/20* (2016.01)
(Continued)

(52) U.S. Cl.
CPC ............... *A61B 6/12* (2013.01); *A61B 6/032* (2013.01); *A61B 6/466* (2013.01); *A61B 6/487* (2013.01);
(Continued)

(58) Field of Classification Search
CPC ........... A61B 6/12; A61B 6/032; A61B 6/466; A61B 6/487; A61B 6/547; A61B 34/20;
(Continued)

(56) References Cited

U.S. PATENT DOCUMENTS 6,373,916 B1 4/2002 Inoue et al.
6,473,634 B1 10/2002 Barni
(Continued)

FOREIGN PATENT DOCUMENTS

BR 0013237 A 7/2003
BR 0116004 A 6/2004
(Continued)

OTHER PUBLICATIONS

Extended European Search Report issued in European Application No. 20195109.2 dated Feb. 22, 2021.

*Primary Examiner* — Colin T. Sakamoto
*Assistant Examiner* — Tommy T Ly
(74) *Attorney, Agent, or Firm* — Weber Rosselli & Cannon LLP (57) ABSTRACT

Imaging systems and methods estimate poses of a fluoroscopic imaging device, which may be used to reconstruct 3D volumetric data of a target area, based on a sequence of fluoroscopic images of a medical device or points, e.g., radiopaque markers, on the medical device captured by performing a fluoroscopic sweep. The systems and methods may identify and track the points along a length of the medical device appearing in the captured fluoroscopic images. The 3D coordinates of the points may be obtained, for example, from electromagnetic sensors or by performing a structure from motion method on the captured fluoroscopic images. In other aspects, a 3D shape of the catheter is determined, then the angle at which the 3D catheter projects onto the 2D catheter in each captured fluoroscopic image is found.

17 Claims, 8 Drawing Sheets

(51) Int. Cl.
  *A61B 6/03*      (2006.01)
  *A61B 6/00*      (2006.01)
  *A61B 90/00*     (2016.01)

(52) U.S. Cl.
  CPC .............. *A61B 6/547* (2013.01); *A61B 34/20* (2016.02); *A61B 90/39* (2016.02); *A61B 2034/2051* (2016.02); *A61B 2034/2055* (2016.02); *A61B 2090/3966* (2016.02)

(58) Field of Classification Search
  CPC ............ A61B 90/39; A61B 2034/2051; A61B 2034/2055; A61B 2090/3966; A61B 2090/376; A61B 5/065; A61M 25/0108
  See application file for complete search history.

(56) References Cited

U.S. PATENT DOCUMENTS

| | | |
|---|---|---|
| 7,551,759 B2 | 6/2009 | Hristov et al. |
| 7,916,918 B2 | 3/2011 | Suri et al. |
| 8,335,359 B2 | 12/2012 | Fidrich et al. |
| 8,482,606 B2 | 7/2013 | Razzaque et al. |
| 8,625,869 B2 | 1/2014 | Harder et al. |
| 8,706,184 B2 | 4/2014 | Mohr et al. |
| 8,827,934 B2 | 9/2014 | Chopra et al. |
| 9,433,390 B2 | 9/2016 | Nathaniel et al. |
| 9,833,167 B2 | 12/2017 | Cohen et al. |
| 9,888,898 B2 | 2/2018 | Imagawa et al. |
| 9,918,659 B2 | 3/2018 | Chopra et al. |
| 10,127,629 B2 | 11/2018 | Razzaque et al. |
| 10,130,316 B2 | 11/2018 | Funabasama et al. |
| 10,373,719 B2 | 8/2019 | Soper et al. |
| 10,376,178 B2 | 8/2019 | Chopra |
| 10,405,753 B2 | 9/2019 | Sorger |
| 10,478,162 B2 | 11/2019 | Barbagli et al. |
| 10,480,926 B2 | 11/2019 | Froggatt et al. |
| 10,524,866 B2 | 1/2020 | Srinivasan et al. |
| 10,555,788 B2 | 2/2020 | Panescu et al. |
| 10,610,306 B2 | 4/2020 | Chopra |
| 10,638,953 B2 | 5/2020 | Duindam et al. |
| 10,674,970 B2 | 6/2020 | Averbuch et al. |
| 10,682,070 B2 | 6/2020 | Duindam |
| 10,706,543 B2 | 7/2020 | Donhowe et al. |
| 10,709,506 B2 | 7/2020 | Coste-Maniere et al. |
| 10,772,485 B2 | 9/2020 | Schlesinger et al. |
| 10,796,432 B2 | 10/2020 | Mintz et al. |
| 10,823,627 B2 | 11/2020 | Sanborn et al. |
| 10,827,913 B2 | 11/2020 | Ummalaneni et al. |
| 10,835,153 B2 | 11/2020 | Rafii-Tari et al. |
| 10,885,630 B2 | 1/2021 | Li et al. |
| 10,896,506 B2 | 1/2021 | Zhao et al. |
| 2003/0013972 A1 | 1/2003 | Makin |
| 2004/0097804 A1* | 5/2004 | Sobe ..................... A61B 34/20 600/424 |
| 2013/0303945 A1 | 11/2013 | Blumenkranz et al. |
| 2014/0035798 A1 | 2/2014 | Kawada et al. |
| 2015/0148690 A1 | 5/2015 | Chopra et al. |
| 2015/0265368 A1 | 9/2015 | Chopra et al. |
| 2016/0157939 A1 | 6/2016 | Larkin et al. |
| 2016/0183841 A1 | 6/2016 | Duindam et al. |
| 2016/0192860 A1 | 7/2016 | Allenby et al. |
| 2016/0287344 A1 | 10/2016 | Donhowe et al. |
| 2017/0035380 A1* | 2/2017 | Barak ..................... A61B 6/56 |
| 2017/0112576 A1 | 4/2017 | Coste-Maniere et al. |
| 2017/0209071 A1 | 7/2017 | Zhao et al. |
| 2017/0258418 A1 | 9/2017 | Averbuch et al. |
| 2017/0265952 A1 | 9/2017 | Donhowe et al. |
| 2017/0311844 A1 | 11/2017 | Zhao et al. |
| 2017/0319165 A1 | 11/2017 | Averbuch |
| 2018/0078318 A1 | 3/2018 | Barbagli et al. |
| 2018/0153621 A1 | 6/2018 | Duindam et al. |
| 2018/0160990 A1* | 6/2018 | Weingarten .......... A61B 6/5235 |
| 2018/0200003 A1* | 7/2018 | Olson .................... A61B 34/20 |
| 2018/0235709 A1 | 8/2018 | Donhowe et al. |
| 2018/0240237 A1 | 8/2018 | Donhowe et al. |
| 2018/0256262 A1 | 9/2018 | Duindam et al. |
| 2018/0263706 A1 | 9/2018 | Averbuch |
| 2018/0279852 A1 | 10/2018 | Rafii-Tari et al. |
| 2018/0325419 A1 | 11/2018 | Zhao et al. |
| 2019/0000559 A1 | 1/2019 | Berman et al. |
| 2019/0000560 A1 | 1/2019 | Berman et al. |
| 2019/0008413 A1 | 1/2019 | Duindam et al. |
| 2019/0038365 A1* | 2/2019 | Soper .................... A61B 6/487 |
| 2019/0065209 A1 | 2/2019 | Mishra et al. |
| 2019/0110839 A1 | 4/2019 | Rafii-Tari et al. |
| 2019/0175062 A1 | 6/2019 | Rafii-Tari et al. |
| 2019/0183318 A1 | 6/2019 | Froggatt et al. |
| 2019/0183585 A1 | 6/2019 | Rafii-Tari et al. |
| 2019/0183587 A1 | 6/2019 | Rafii-Tari et al. |
| 2019/0192234 A1 | 6/2019 | Gadda et al. |
| 2019/0209016 A1 | 7/2019 | Herzlinger et al. |
| 2019/0209043 A1 | 7/2019 | Zhao et al. |
| 2019/0216548 A1 | 7/2019 | Ummalaneni |
| 2019/0239723 A1 | 8/2019 | Duindam et al. |
| 2019/0239831 A1 | 8/2019 | Chopra |
| 2019/0239838 A1* | 8/2019 | Barak ..................... G06T 7/251 |
| 2019/0250050 A1 | 8/2019 | Sanborn et al. |
| 2019/0254649 A1 | 8/2019 | Walters et al. |
| 2019/0269470 A1 | 9/2019 | Barbagli et al. |
| 2019/0272634 A1 | 9/2019 | Li et al. |
| 2019/0298160 A1 | 10/2019 | Ummalaneni et al. |
| 2019/0298451 A1 | 10/2019 | Wong et al. |
| 2019/0320878 A1 | 10/2019 | Duindam et al. |
| 2019/0320937 A1 | 10/2019 | Duindam et al. |
| 2019/0336238 A1 | 11/2019 | Yu et al. |
| 2019/0343424 A1 | 11/2019 | Blumenkranz et al. |
| 2019/0350659 A1 | 11/2019 | Wang et al. |
| 2019/0365199 A1 | 12/2019 | Zhao et al. |
| 2019/0365479 A1 | 12/2019 | Rafii-Tari |
| 2019/0365486 A1 | 12/2019 | Srinivasan et al. |
| 2019/0380787 A1 | 12/2019 | Ye et al. |
| 2020/0000319 A1 | 1/2020 | Saadat et al. |
| 2020/0000526 A1 | 1/2020 | Zhao |
| 2020/0008655 A1 | 1/2020 | Schlesinger et al. |
| 2020/0030044 A1 | 1/2020 | Wang et al. |
| 2020/0030461 A1 | 1/2020 | Sorger |
| 2020/0038750 A1 | 2/2020 | Kojima |
| 2020/0043207 A1 | 2/2020 | Lo et al. |
| 2020/0046431 A1 | 2/2020 | Soper et al. |
| 2020/0046436 A1 | 2/2020 | Tzeisler et al. |
| 2020/0054399 A1 | 2/2020 | Duindam et al. |
| 2020/0060771 A1 | 2/2020 | Lo et al. |
| 2020/0069192 A1 | 3/2020 | Sanborn et al. |
| 2020/0077870 A1 | 3/2020 | Dicarlo et al. |
| 2020/0078095 A1 | 3/2020 | Chopra et al. |
| 2020/0078103 A1 | 3/2020 | Duindam et al. |
| 2020/0085514 A1 | 3/2020 | Blumenkranz |
| 2020/0109124 A1 | 4/2020 | Pomper et al. |
| 2020/0129045 A1 | 4/2020 | Prisco |
| 2020/0129239 A1 | 4/2020 | Bianchi et al. |
| 2020/0138515 A1 | 5/2020 | Wong |
| 2020/0155116 A1 | 5/2020 | Donhowe et al. |
| 2020/0170623 A1 | 6/2020 | Averbuch |
| 2020/0170720 A1 | 6/2020 | Ummalaneni |
| 2020/0179058 A1 | 6/2020 | Barbagli et al. |
| 2020/0188038 A1 | 6/2020 | Donhowe et al. |
| 2020/0205903 A1 | 7/2020 | Srinivasan et al. |
| 2020/0205904 A1 | 7/2020 | Chopra |
| 2020/0214664 A1 | 7/2020 | Zhao et al. |
| 2020/0229679 A1 | 7/2020 | Zhao et al. |
| 2020/0242767 A1 | 7/2020 | Zhao et al. |
| 2020/0275860 A1 | 9/2020 | Duindam |
| 2020/0297442 A1 | 9/2020 | Adebar et al. |
| 2020/0315554 A1 | 10/2020 | Averbuch et al. |
| 2020/0330795 A1 | 10/2020 | Sawant et al. |
| 2020/0352427 A1 | 11/2020 | Deyanov |
| 2020/0364865 A1 | 11/2020 | Donhowe et al. |
| 2021/0052314 A1* | 2/2021 | Holsing .................. A61B 8/12 |

FOREIGN PATENT DOCUMENTS

| | | |
|---|---|---|
| CZ | 486540 | 9/2016 |
| CZ | 2709512 | 8/2017 |
| CZ | 2884879 | 1/2020 |

(56) References Cited

FOREIGN PATENT DOCUMENTS

| | | | |
|---|---|---|---|
| EP | 3524157 | A1 | 8/2019 |
| EP | 3413830 | A4 | 9/2019 |
| EP | 3478161 | A4 | 2/2020 |
| EP | 3641686 | A2 | 4/2020 |
| EP | 3644885 | A1 | 5/2020 |
| EP | 3644886 | A1 | 5/2020 |
| MX | PA03005028 | A | 1/2004 |
| MX | 225663 | B | 1/2005 |
| MX | 226292 | | 2/2005 |
| MX | 246862 | B | 6/2007 |
| MX | 265247 | | 3/2009 |
| MX | 284569 | B | 3/2011 |
| WO | 2018078445 | A2 | 5/2018 |

* cited by examiner

SYSTEMS AND METHODS FOR POSE ESTIMATION OF A FLUOROSCOPIC IMAGING DEVICE AND FOR THREE-DIMENSIONAL IMAGING OF BODY STRUCTURES

CROSS-REFERENCE TO RELATED APPLICATION

The present application claims the benefit of and priority to U.S. Provisional Patent Application Ser. No. 62/897,760, filed on Sep. 9, 2019, the entire content of which is incorporated herein by reference.

FIELD

This disclosure relates to the field of imaging, and particularly to the estimation of a pose of an imaging device and to three-dimensional imaging of body structures.

BACKGROUND

A fluoroscopic imaging device is commonly located in the operating room during procedures to navigate a medical device to a target within a patient's body. The fluoroscopic imaging device may be used by a clinician, for example, to visualize and confirm the placement of a medical device while it is being navigated to a desired location or after it has been navigated to a desired location. Although standard fluoroscopic images display highly dense objects such as metal tools and bones as well as large soft-tissue objects such as the heart, the fluoroscopic images have difficulty resolving small soft-tissue objects of interest, such as lesions, which are to be ablated. Furthermore, the fluoroscope image is only a two-dimensional projection, while in order to accurately and safely navigate within the body, 3D imaging is needed.

Therefore, a fast, accurate, and robust three-dimensional reconstruction of structures based on fluoroscopic imaging performed during medical procedures is needed.

SUMMARY

In one aspect, this disclosure features a method for estimating a pose of a fluoroscopic imaging device. The method includes performing a sweep with the fluoroscopic imaging device to capture fluoroscopic images of a catheter. The method also includes identifying and tracking radiopaque markers along a length of a catheter in the fluoroscopic images of the catheter. The method also includes determining three-dimensional (3D) coordinates of the catheter based on the tracked radiopaque markers. The method also includes estimating the pose of the fluoroscopic imaging device based on the 3D coordinates of the catheter.

In aspects, implementations of this disclosure may include one or more of the following features. The radiopaque markers may be tracking sensors. The tracking sensors may be coils. The sweep may be a wide sweep including fluoroscopic imaging device viewing angles about a longitudinal axis of greater than 30 degrees with respect to an anteroposterior position.

In another aspect, this disclosure features a method that includes performing a sweep with a fluoroscopic imaging device to capture fluoroscopic images of a patient's body. The method also includes identifying and tracking radiopaque markers along a length of a catheter in the fluoroscopic images of the catheter advancing through a patient's body. The method also includes performing a 3D structure from motion method on the tracked radiopaque markers to estimate a three-dimensional (3D) structure of the catheter and the pose of the fluoroscopic imaging device. In some aspects, the method also includes constructing 3D volumetric data of an area based on the estimated poses of the fluoroscopic imaging device.

In another aspect, this disclosure features a method for estimating a pose of a fluoroscopic imaging device. The method includes determining a three-dimensional (3D) shape of a catheter. The method also includes performing a sweep with the fluoroscopic imaging device to capture fluoroscopic images of the catheter in a patient's body. The method also includes for each fluoroscopic image of the fluoroscopic images, estimating a pose at which the 3D shape of the catheter projects onto a catheter in each fluoroscopic image.

In aspects, implementations of this disclosure may include one or more of the following features. The sweep may be a wide sweep including fluoroscopic imaging device viewing angles about a longitudinal axis of the patient's body greater than 50 degrees with respect to an anteroposterior position. The catheter may include at least one fiber-optic sensor disposed along a length of the catheter and the 3D shape of the catheter may be determined by performing a 3D shape sensing method based on fiber-optic sensor signals obtained from the at least one fiber-optic sensor. Determining the 3D shape of the catheter may include performing a structure from motion process on the fluoroscopic images to estimate a first 3D shape of the catheter, determining a body structure in which the catheter is disposed, determining a 3D shape of the body structure in which the catheter is disposed, determining a second 3D shape of the catheter based on the 3D shape of the body structure in which the catheter is disposed, estimating the 3D shape of the catheter based on the first 3D shape and the second 3D shape. The 3D shape of the body structure in which the catheter is disposed may be determined based on computed tomography (CT) images of the body structure in which the catheter is disposed. The body structure may be an airway of a lung.

In aspects, the fluoroscopic images may include first fluoroscopic images of the catheter and second fluoroscopic images of the catheter and a structure of markers, and determining the 3D shape of the catheter may include estimating the pose of the fluoroscopic imaging device for each image of the second fluoroscopic images based on a projection of the structure of markers on each image of the second fluoroscopic images and reconstructing the 3D shape of the catheter based on the estimated poses of the fluoroscopic imaging device. The structure of markers may be a grid of markers. The second fluoroscopic images may correspond to fluoroscopic imaging device viewing angles around a longitudinal axis of the patient's body of less than 30 degrees with respect to an anteroposterior position.

In another aspect, this disclosure features a method for constructing fluoroscopic-based three-dimensional volumetric data of a target area within a patient's body. The method includes performing a sweep with a fluoroscopic imaging device to acquire a sequence of fluoroscopic images of the target area and of radiopaque markers of a medical device. The method also includes identifying and tracking the radiopaque markers along a length of a medical device in the sequence of fluoroscopic images of the medical device advancing through a patient's body. The method also includes determining three-dimensional (3D) coordinates of the medical device based on the tracked the radiopaque markers. The method also includes estimating angles of the fluoroscopic imaging device based on the 3D coordinates of the medical device. The method also includes constructing fluoroscopic-based 3D volumetric data of the target area based on the estimated angles of the fluoroscopic imaging device.

In aspects, implementations of this disclosure may include one or more of the following features. The method may also include determining an offset between the medical device and the target area based on the fluoroscopic-based three-dimensional volumetric data. The method may also include facilitating navigation of the medical device to the target area using a locating system indicating the location of the medical device in a display. The method may also include correcting a display of the location of the medical device with respect to the target area based on the determined offset between the medical device and the target area. The locating system may be an electromagnetic locating system. The method may also include displaying a 3D rendering of the target area on the display. The method may also include registering the locating system to the 3D rendering. Correcting the location of the medical device with respect to the target area includes updating registration of the locating system to the 3D rendering. The method may also include generating the 3D rendering of the target area based on previously-acquired CT volumetric data of the target area. The target area may include at least a portion of lungs and the medical device may be navigated to the target area through an airways luminal network. The target area may include at least a portion of the lungs. The target area may include a soft tissue target. The target area may include a target to be ablated.

BRIEF DESCRIPTION OF THE DRAWINGS

Various exemplary aspects are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. The figures are listed below.

DETAILED DESCRIPTION

This disclosure relates to improved fluoroscopic navigation systems and methods that are sufficient for procedures that require accurate and robust three-dimensional (3D) imaging, e.g., biopsy and ablation procedures. In some cases, lesions may smear in the fluoroscopic images and the shape of the lesion may not be accurate in the fluoroscopic images. For example, fluoroscopic images may not be sufficient to determine that an ablation kill zone will completely cover a lesion. If there is a fluoroscopic imaging sweep wider than 50 degrees around an anteroposterior (AP) position, the image quality improves so that it is sufficient for accurately and safely performing ablation procedures. As the fluoroscopic imaging sweep approaches 180 degrees around the AP position, the image quality may approach the image quality that is attainable with a cone beam computed tomography system.

For some beds or operating tables, e.g., those that do not include bars or include bars that can be adjusted, a fluoroscopic imaging device can be mechanically rotated more than 50 degrees about an AP position. However, the projection of a grid of markers, which is disposed beneath the patient and used to estimate the pose of the fluoroscopic imaging device, may disappear from the fluoroscopic images when the fluoroscopic imaging device is positioned too lateral with respect to the patient's body, e.g., the fluoroscopic imaging device view is at an angle of greater than 75 degrees with respect to the AP position. For example, when a patient has an anterior lesion and the fluoroscopic imaging device is rotated towards a lateral view position, the grid of markers begins to disappear from the fluoroscopic images and only the body of the patient appears in the fluoroscopic images.

According to aspects of this disclosure, an angle measurement of a fluoroscopic imaging device with respect to a target area is needed for the 3D reconstruction of the structures within the target area. In some aspects, a medical device such as a catheter or markers disposed thereon are used by fluoroscopic-based systems and methods to estimate the pose of a fluoroscopic imaging device while capturing fluoroscopic images of a patient's body. The estimated poses may then be used to reconstruct 3D volumetric data of a target area. The systems and methods may track points, e.g., radiopaque markers, along a length of the medical device appearing in the captured fluoroscopic images. The 3D coordinates of the points may be obtained, for example, from electromagnetic sensors or by performing a structure from motion method on the captured fluoroscopic images. In aspects, the shape of the catheter is determined in 3D, then, for each captured fluoroscopic image, the angle in which the 3D catheter projects onto the 2D catheter is found. The 3D shape of the catheter may be determined based on the shape of the body structure in which the medical device or catheter is disposed.

In some aspects, the systems and methods of this disclosure use the shape of the catheter from the part of the fluoroscopic video images where the grid of markers can be seen in the fluoroscopic video images. From the 3D reconstruction based on those fluoroscopic video images, the 3D shape of the catheter can be extracted. For every other frame of the fluoroscopic video that is too lateral to see the grid of markers, the shape of the catheter can still be seen in the images. Thus, according to the shape of the catheter on the projected image and the 3D shape of the catheter, the angle of the view of the fluoroscopic imaging device with respect to the catheter can be determined based on the frames of fluoroscopic video that are too lateral to see the grid of markers.

Fiducials (e.g., markers) may be placed on the catheter or the overall or entire shape of the catheter can be used. The fiducials may be radiopaque rings disposed along a length of a catheter a predetermined distance from each other, e.g., 1cm, 1.5 cm, 2 cm, etc. The 3D shape of the catheter may be reconstructed from a narrow sweep, e.g., 50 degrees, about the AP view, and then the 3D positions of the radiopaque rings may be detected along the catheter. Then, a system of this disclosure may solve for the other angles where the grid of markers is not seen from a wide sweep, e.g., a sweep between 160 and 180 degrees about the AP position, based on the 3D positions of the radiopaque rings or other suitable markers.

Figure 1A:
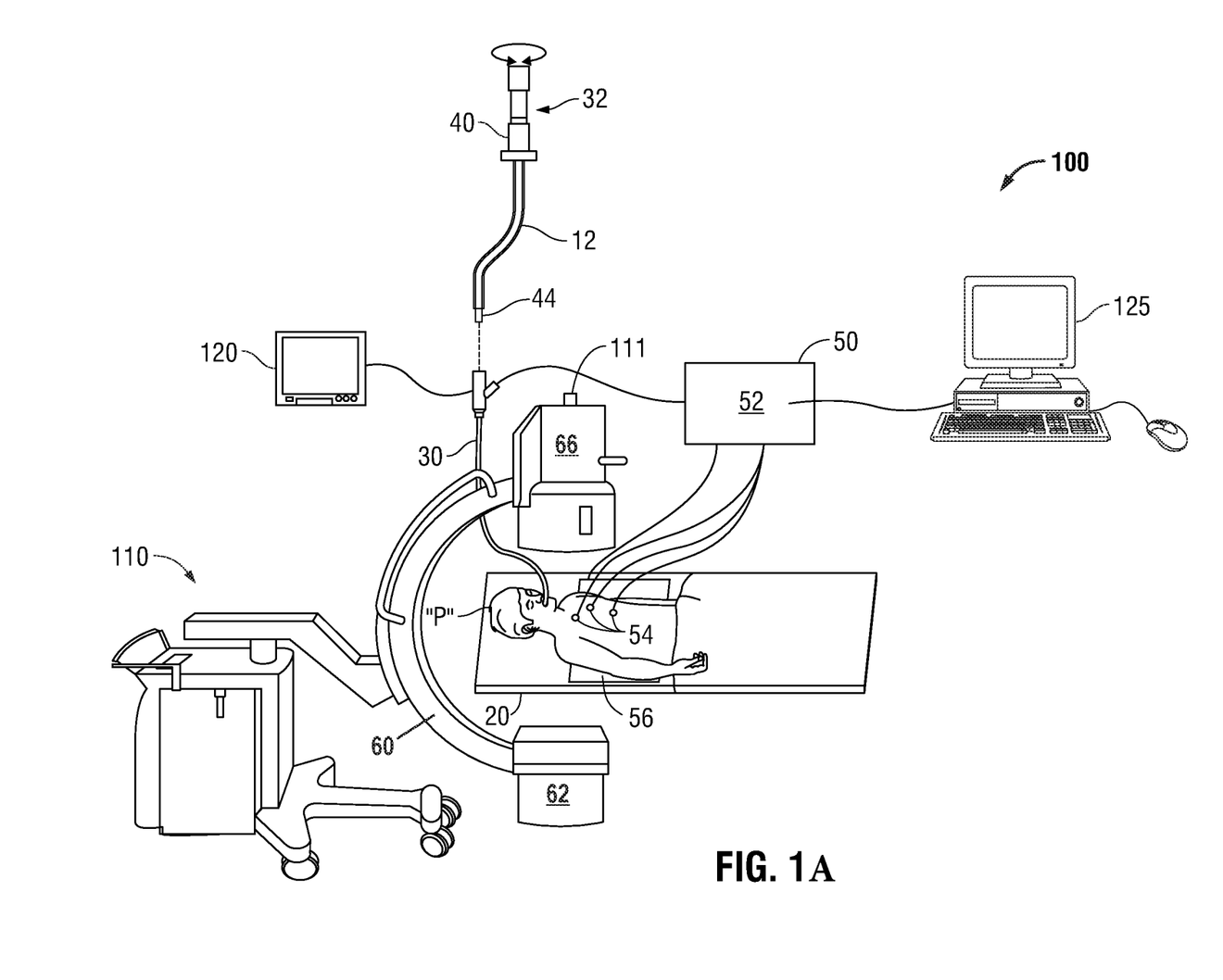
FIG. 1A is a schematic diagram of an exemplary system for constructing fluoroscopic-based three-dimensional volumetric data in accordance with aspects of this disclosure.

FIG. 1A depicts an aspect of an Electromagnetic Navigation (EMN) system 100 that may be used in aspects of the systems and methods of this disclosure. The EMN system 100 is configured for reviewing CT image data to identify one or more targets, planning a pathway to an identified target (planning phase), navigating a catheter 12 of a catheter guide assembly 40 to a target (navigation phase) via a user interface, and confirming placement of the catheter 12 (or any portion of the catheter guide assembly 40 or any instruments inserted therethrough) relative to the target. One such electromagnetic navigation system is the ELECTROMAGNETIC NAVIGATION BRONCHOSCOPY® system currently sold by Medtronic PLC. The target may be tissue of interest, e.g., tissue to be ablated, or a region of interest identified during review of the CT image data during the planning phase. Following navigation, a medical instrument such as a biopsy tool, delivery device, or treatment device may be inserted into the catheter 12 to obtain a tissue sample from the tissue located at, or proximate to, the target, deliver items or therapies to the region, or treat the region.

As shown in FIG. 1A, catheter 12 is part of a catheter guide assembly 40 which extends distally from a handle 41 of the catheter guide assembly 40. In practice, the catheter 12 may be inserted into bronchoscope 30 for access to a luminal network of the patient "P." Specifically, catheter 12 of catheter guide assembly 40 may be inserted into a working channel of bronchoscope 30 for navigation through a patient's luminal network. A locatable guide (LG) 32, including a sensor 44 disposed thereon, is inserted into the catheter 12 and locked into position such that the sensor 44 extends a desired distance beyond the distal tip of the catheter 12. The position and orientation of the sensor 44 relative to a reference coordinate system, and thus the distal end of the catheter 12, within an electromagnetic field can be derived.

Catheter guide assemblies 40 are currently marketed and sold by Medtronic PLC under the brand names SUPERDIMENSION® Procedure Kits, or EDGE™ Procedure Kits, and are contemplated as useable with this disclosure.

EMN system 100 generally includes an operating table 20 configured to support a patient "P;" a bronchoscope 30 configured for insertion through the patient "P's" mouth into the patient "P's" airways; monitoring equipment 120 coupled to bronchoscope 30 (e.g., a video display, for displaying the video images received from the video imaging system of bronchoscope 30); a tracking system 50 including a tracking module 52, a plurality of reference sensors 54 and a transmitter mat 56; and a computing device 125 including software and/or hardware used to facilitate identification of a target, pathway planning to the target, navigation of a medical device or instrument to the target, and confirmation of placement of a catheter 12, or a suitable device therethrough, relative to the target.

A fluoroscopic imaging device 110 capable of acquiring fluoroscopic or x-ray images or video of the patient "P" is also included in aspects of system 100. The fluoroscopic images, series of images, or video captured by the fluoroscopic imaging device 110 may be stored within the fluoroscopic imaging device 110 or transmitted to computing device 125 for storage, processing, and display as described in more detail herein. Additionally, the fluoroscopic imaging device 110 may move relative to the patient "P" so that images may be acquired from different angles or perspectives relative to the patient "P" to create fluoroscopic video. In one aspect of this disclosure, fluoroscopic imaging device 110 includes an angle measurement device 111 which is configured to measure the angle of the fluoroscopic imaging device 110 relative to the patient "P." Angle measurement device 111 may be an accelerometer.

Fluoroscopic imaging device 110 may include one or more imaging devices. In aspects including multiple imaging devices, each imaging device may be a different type of imaging device or the same type. In aspects, the fluoroscopic imaging device 110 is a C-mount fluoroscope based on a C-arm 60. At one end of the C-arm 60 is an X-ray source 62 that includes an X-ray tube and a collimator (not shown). At the other end of the C-arm 60 is an X-ray detector 66 that includes an anti-scatter grid, an image intensifier, and a CCD camera (not shown). The collimator blocks the X-rays emerging from X-ray tube except at an aperture (not shown). A cone of X-rays emerges from the aperture and impinges on the anti-scatter grid and the image intensifier of the X-ray detector 66. The image created in the image intensifier is captured by the CCD camera. Depending on the spatial density distribution in an object such as a patient that is traversed by the cone, each element of the CCD array of the CCD camera receives more or less light from the image intensifier, and the corresponding pixel of the image produced by the C-mount fluoroscope is correspondingly darker or lighter.

Computing device 125 may be any suitable computing device including a processor and storage medium, wherein the processor is capable of executing instructions stored on the storage medium. The computing device 125 is operably coupled to some or all of the components of system 100 including bronchoscope 30, catheter guide assembly 40, locatable guide 32, and tracking system 50. The computing device 125 may include a database configured to store patient data, CT data sets including CT images and volumetric renderings, fluoroscopic data sets including fluoroscopic images and video, navigation plans, and any other such data. Although not explicitly illustrated, the computing device 125 may include inputs, or may otherwise be configured to receive, CT data sets, fluoroscopic images or video, and other data described herein. Additionally, computing device 125 includes a display configured to display graphical user interfaces. Computing device 125 may be connected to one or more networks through which one or more databases may be accessed.

With respect to the planning phase, computing device 125 utilizes previously acquired CT image data for generating and viewing a three-dimensional model of the patient's "P's" airways, enables the identification of a target on the three-dimensional model (automatically, semi-automatically, or manually), and allows for determining a pathway through the patient's "P's" airways to tissue located at and around the target. More specifically, CT images acquired from previous CT scans are processed and assembled into a three-dimensional CT volume, which is then utilized to generate a three-dimensional model of the patient's "P's" airways.

The three-dimensional model may be displayed on a display associated with computing device 125, or in any other suitable fashion. Using computing device 125, various views of the three-dimensional model or two-dimensional images generated from the three-dimensional model are presented. The three-dimensional model may be manipulated to facilitate identification of target on the three-dimensional model or two-dimensional images, and selection of a suitable pathway through the patient's "P's" airways to access tissue located at the target. Once selected, the pathway plan, three-dimensional model, and images derived therefrom, can be saved and exported to a navigation system for use during one or more navigation phases. One such planning software is the ILOGIC® planning suite currently sold by Medtronic PLC.

With respect to the navigation phase, a six degrees-of-freedom electromagnetic tracking system 50 or other suitable positioning measuring system may be utilized for performing registration of the images and the pathway for navigation, although other configurations are also contemplated. Tracking system 50 includes a tracking module 52, a reference sensors 54, and a transmitter mat 56. Tracking system 50 is configured for use with a locatable guide 32 and sensor 44. As described above, locatable guide 32 and sensor 44 are configured for insertion through a catheter 12 into a patient "P's" airways (either with or without bronchoscope 30) and are selectively lockable relative to one another via a locking mechanism.

Transmitter mat 56 is positioned beneath patient "P." Transmitter mat 56 generates an electromagnetic field around at least a portion of the patient "P" within which the position of a plurality of reference sensors 54 and the sensor element 44 can be determined with use of a tracking module 52. The transmitter mat 56 may include a structure or grid of at least partially radiopaque markers, which are used in some aspects of this disclosure to determine the 3D shape of a medical device or catheter being guided towards a target. In some aspects, one or more of reference sensors 54 are attached to the chest of the patient "P" in addition to the transmitter mat 56. In other aspects, only the mat is utilized. The six degrees of freedom coordinates of reference sensors 54 are sent to computing device 125 (which includes the appropriate software) where they are used to calculate a patient coordinate frame of reference.

Registration is generally performed to coordinate locations of the three-dimensional model and two-dimensional images from the planning phase with the patient's "P's" airways as observed through the bronchoscope 30, and allow for the navigation phase to be undertaken with precise knowledge of the location of the sensor 44, even in portions of the airway where the bronchoscope 30 cannot reach. Other suitable registration techniques and their implementation in luminal navigation are also contemplated by this disclosure.

Registration of the patient "P's" location on the transmitter mat 56 is performed by moving locatable guide 32 through the airways of the patient "P." More specifically, data pertaining to locations of sensor 44, while locatable guide 32 is moving through the airways, is recorded using transmitter mat 56, reference sensors 54, and tracking module 52. A shape resulting from this location data is compared to an interior geometry of passages of the three-dimensional (3D) model generated in the planning phase, and a location correlation between the shape and the 3D model based on the comparison is determined, e.g., utilizing the software on computing device 125. Other registration methods are contemplated by this disclosure including, for example, fluoroscopic registration with the 3D model, shape matching, and other suitable techniques for registering operative images of anatomical features to preoperative images of those same anatomical features. In aspects, these other registration methods may or may not utilize the sensor 44 to perform registration.

In addition, the software identifies non-tissue space (e.g., air-filled cavities) in the three-dimensional model. The software aligns, or registers, an image representing a location of sensor 44 with the three-dimensional model and two-dimensional images generated from the three-dimension model, which are based on the recorded location data and an assumption that locatable guide 32 remains located in non-tissue space in the patient "P's" airways. Alternatively, a manual registration technique may be employed by navigating the bronchoscope 30 with the sensor 44 to pre-specified locations in the lungs of the patient "P", and manually correlating the images from the bronchoscope to the model data of the three-dimensional model.

Following registration of the patient "P" to the image data and pathway plan, a user interface is displayed in the navigation software of system 100 which sets for the pathway that the clinician is to follow to reach the target. One such navigation software is the ILOGIC® navigation suite currently sold by Medtronic PLC.

Once catheter 12 has been successfully navigated proximate the target as depicted on the user interface, the locatable guide 32 may be unlocked from catheter 12 and removed, leaving catheter 12 in place as a guide channel for guiding medical instruments. Such medical instruments may include, without limitation, optical systems, ultrasound probes, marker placement tools, biopsy tools, ablation tools (i.e., microwave ablation devices), laser probes, cryogenic probes, sensor probes, and aspirating needles.

The three-dimensional model of a patient's lungs, generated from previously acquired CT scans, may not provide a basis sufficient for accurate guiding of the catheter 12 of the catheter guide assembly 40 to a target during the procedure. As described above, the inaccuracy may be caused by CT-to-Body divergence (deformation of the patient's lungs during the procedure relative to the lungs at the time of the acquisition of the previously acquired CT data). Thus, another imaging modality is necessary to visualize targets and/or a terminal bronchial branch, and enhance the electromagnetic navigation procedure by correcting the navigation during the procedure, enabling visualization of the target, and confirming placement of the medical or surgical device during the procedure. For this purpose, the system described herein processes and converts image data captured by the fluoroscopic imaging device 110 to a 3D reconstruction of the target area as is described herein. This fluoroscopic image data may be utilized to identify such targets and terminal bronchial branches or be incorporated into, and used to update, the data from the CT scans in an effort to provide a more accurate navigation procedure. Further, the fluoroscopic images may be captured post-navigation and thus include visuals of the catheter 12 and any medical devices positioned therethrough relative to the target.

Figure 1B:
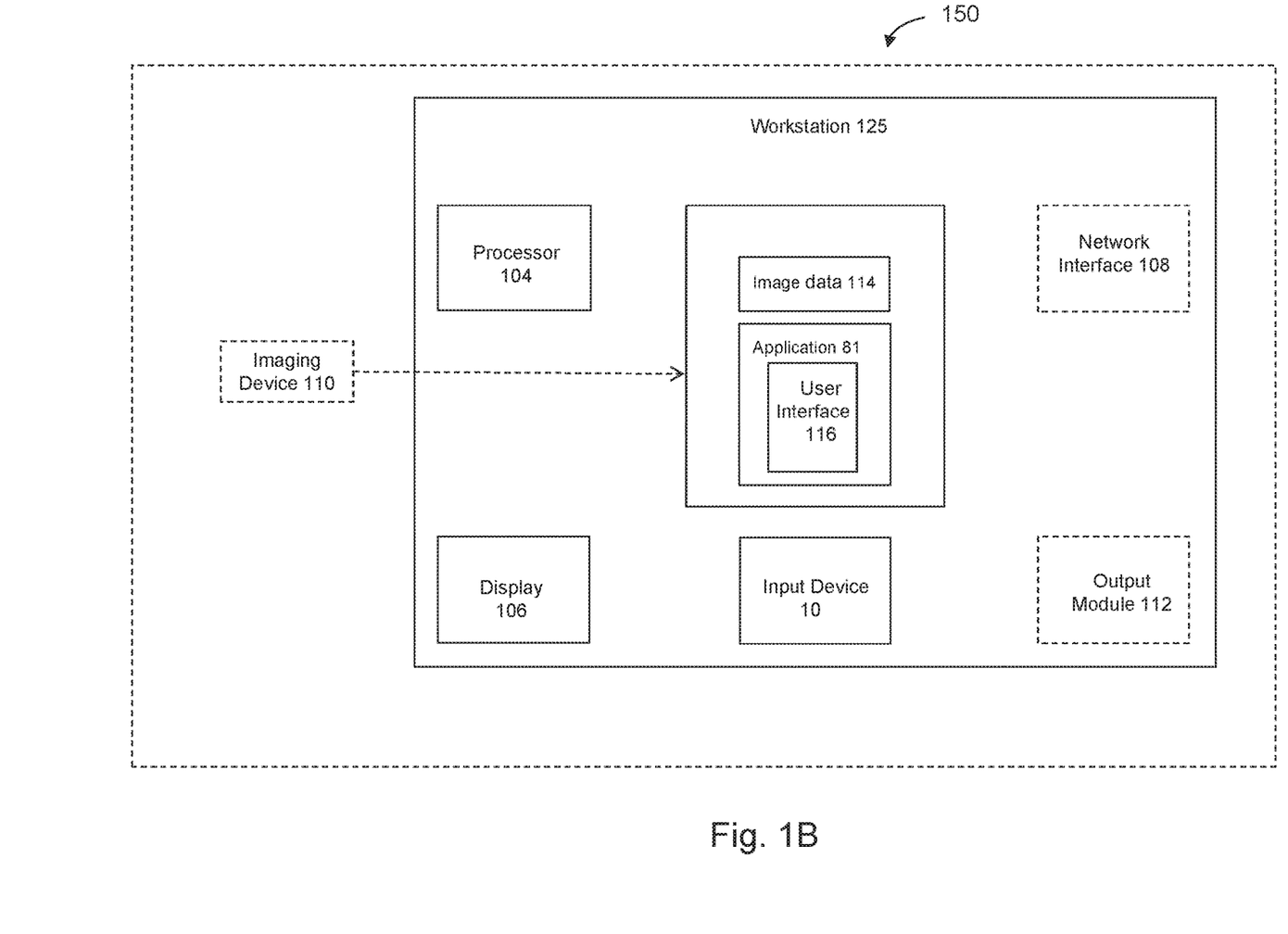
FIG. 1B is a schematic diagram of a system configured for use with the aspects of this disclosure.

Reference is now made to FIG. 1B, which is a schematic diagram of a system 150 configured for use with the methods of FIGS. 3-6 and as described herein. System 150 may include the workstation 125 of FIG. 1A and a fluoroscopic imaging device or fluoroscope 110 of FIG. 1A. In some aspects, workstation 125 may be coupled with fluoroscope 110, directly or indirectly, e.g., by wireless communication. Workstation 125 may include memory 102 (e.g., a storage device), a processor 104, a display 106, and an input device 10. Processor 104 may include one or more hardware processors. Workstation 125 may optionally include an output module 112 and a network interface 108.

Memory 102 may store an application 81 and image data 114 including fluoroscopic imaging data. Application 81 may include instructions executable by processor 104 for, among other functions, executing the methods of this disclosure including the methods of FIGS. 3-6 described herein. Application 81 may further include a user interface 116. Image data 114 may include the 3D imaging data such as a pre-operative CT scan, the fluoroscopic three-dimensional reconstructions (F3DRs) of the target area, and/or any other fluoroscopic image data and/or one or more virtual fluoroscopy images. Processor 104 may be coupled with memory 102, display 106, input device 10, output module 112, network interface 108, and fluoroscopic imaging device 110. Workstation 125 may be a stationary computing device, such as a personal computer, or a portable computing device such as a tablet computer. Workstation 125 may embed multiple computer devices.

Memory 102 may include any non-transitory computer-readable storage media for storing data and/or software including instructions that are executable by processor 204 and which control the operation of workstation 80 and in some aspects, may also control the operation of fluoroscope 110. Fluoroscope 110 is used to capture a sequence of fluoroscopic images based on which the F3DR is generated. The two-dimensional fluoroscopic images in which the medical device is selected may be selected from the captured sequence of fluoroscopic images. In an aspect, storage device or memory 102 may include one or more storage devices such as solid-state storage devices such as flash memory chips. Alternatively, or in addition to the one or more solid-state storage devices, memory 102 may include one or more mass storage devices connected to the processor 104 through a mass storage controller (not shown) and a communications bus (not shown).

Although the description of computer-readable media contained herein refers to a solid-state storage, it should be appreciated by those skilled in the art that computer-readable storage media can be any available media that can be accessed by the processor 104. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by workstation 125.

Application 81 may, when executed by processor 104, cause display 106 to present user interface 116. User interface 116 may be configured to present to the user the F3DR, two-dimensional fluoroscopic images, images of the 3D imaging, and a virtual fluoroscopy view. User interface 116 may be further configured to direct the user to select the target by, among other things, identifying and marking the target in the displayed F3DR or any other fluoroscopic image data in accordance with this disclosure.

Network interface 108 may be configured to connect to a network such as a local area network (LAN) consisting of a wired network and/or a wireless network, a wide area network (WAN), a wireless mobile network, a Bluetooth network, and/or the internet. Network interface 108 may be used to connect between workstation 125 and fluoroscope 110. Network interface 108 may be also used to receive image data 114. Input device 10 may be any device by means of which a user may interact with workstation 125, such as, for example, a mouse, keyboard, foot pedal, touch screen, and/or voice interface. Output module 112 may include any connectivity port or bus, such as, for example, parallel ports, serial ports, universal serial busses (USB), or any other similar connectivity port known to those skilled in the art.

Figure 2A:
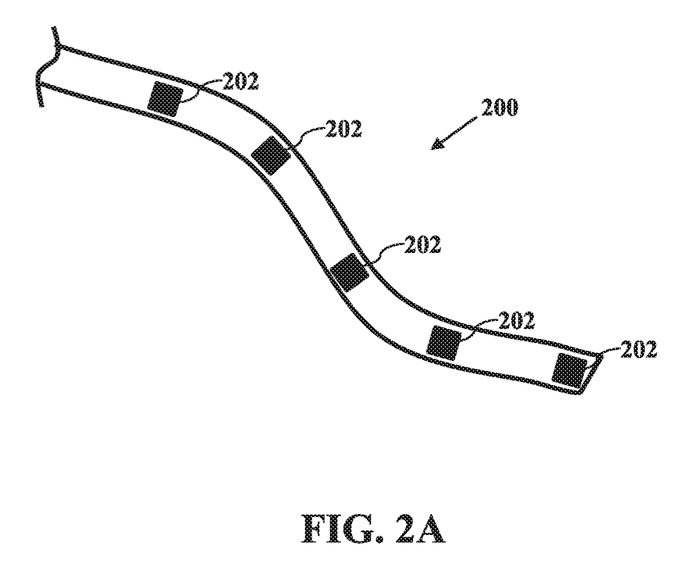
FIG. 2A is a schematic diagram of a catheter configured for use with the aspects of this disclosure.
Figure 2B:
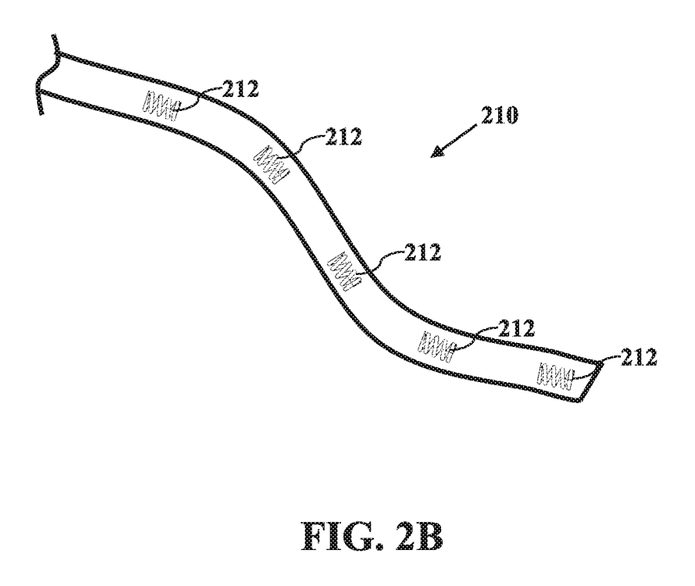
FIG. 2B is a schematic diagram of another catheter configured for use with the aspects of this disclosure.

With reference to FIGS. 2A and 2B, flexible catheters 200, 210 configured for use with the systems and methods of this disclosure are shown. Flexible catheter 200 includes multiple radiopaque markers 202 that may be captured in fluoroscopic images and used to reconstruct the 3D shape of the catheter 200, which, in turn, may be used to estimate the pose of the fluoroscopic imaging device 110 of FIGS. 1A and 1B. In other aspects, flexible catheter 210 includes multiple radiopaque coils 212 that may be used to determine the position of the radiopaque coils in 3D space, which may be used to reconstruct the 3D shape of the catheter 200, which, in turn, may be used to estimate the pose of the fluoroscopic imaging device 110 of FIGS. 1A and 1B. In aspects, although the flexible catheters 200, 210 shown in FIGS. 2A and 2B include five radiopaque markers 202 and coils 212, respectively, the flexible catheters 200, 210 may include any number of radiopaque markers 202 and coils 212, respectively, suitable for reconstructing the 3D shape of the catheters 200, 210 (e.g., three, four, or six radiopaque markers 202 or coils 212).

Figure 3:
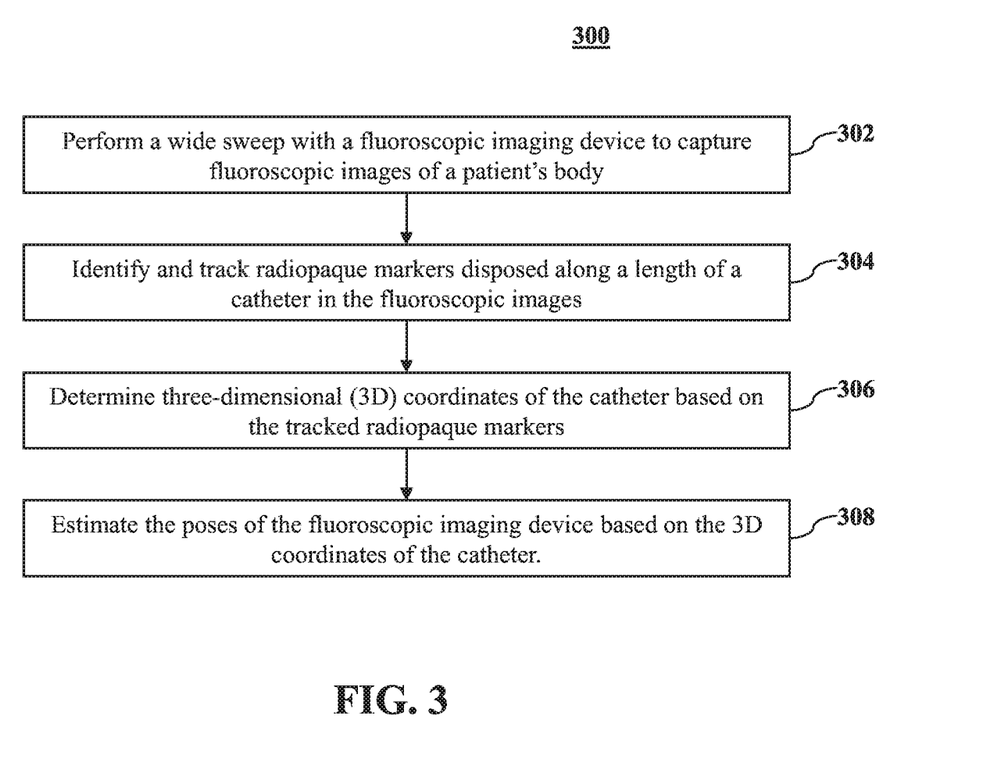
FIG. 3 is a flow chart of a method for estimating the pose of a fluoroscopic imaging device in accordance with aspects of this disclosure.

With reference to FIG. 3, a flow chart of a method 300 for estimating poses of a fluoroscopic imaging device while capturing fluoroscopic images of a patient's body is provided. In aspects, the estimated poses may be used to reconstruct 3D volumetric data of a target area of the patient's body as described herein. At block 302, a sweep with a fluoroscopic imaging device is performed to capture fluoroscopic images of the patient's body. In some aspects, the sweep includes fluoroscopic imaging device viewing angles about a longitudinal axis of the patient's body of greater than 30 degrees with respect to an anteroposterior position. At block 304, radiopaque markers disposed along a length of a catheter in the fluoroscopic images are identified and tracked. In aspects, the radiopaque markers may be identified and tracked as the fluoroscopic sweep is being performed at block 302. In some aspects, the radiopaque markers include disposed along a length of the catheter as illustrated in FIG. 2A.

The radiopaque markers may take any form suitable for identifying and tracking the radiopaque markers in the fluoroscopic images. For example, the radiopaque markers may be in the shape of a rings, a spiral, squares, dots, or other suitable symbols or shapes disposed around the catheter. For example, rings may be equally-spaced a predetermined distance from each other. The predetermined distance may be a suitable distance for accurately determining the 3D positions of the catheter. Alternatively, the rings may not be equally-spaced from each other. In some aspects, the radiopaque markers may be disposed at different axial positions around the catheter to facilitate recognition of the shape of the catheter. In other aspects, the radiopaque markers include coils disposed along a length of the catheter as illustrated in FIG. 2B. In still other aspects, the catheter may be at least partially made of a radiopaque material or coated with a radiopaque material and image processing techniques may be employed to track points on the radiopaque catheter.

In further aspects, the catheter may include both radiopaque markers or material and tracking or electromagnetic (EM) sensors disposed along a portion of the catheter's length. In aspects, the tracking module 52 of the tracking system 50 may be electrically or wirelessly coupled to and in communication with the coils and/or EM sensors disposed along the length of the catheter. In this configuration, the tracking module 52 may activate the transmitter mat 56 and collect data from the coils or EM sensors, which can be used to determine the 3D positions of the tracking sensors, EM sensors, or coils disposed along the length of the catheter. The 3D position information may then be used to determine the 3D shape of the catheter.

At block 306, three-dimensional (3D) coordinates of the catheter are determined based on the radiopaque markers tracked in the two-dimensional fluoroscopic images. And then, at block 308, the poses or angles of the fluoroscopic imaging device with respect to the catheter is estimated based on the 3D coordinates of the catheter using an estimation algorithm or process. The estimation process may include solving a system of linear equations, which describe the connection between the 3D coordinates and the 2D coordinates in the fluoroscopic images.

Figure 4:
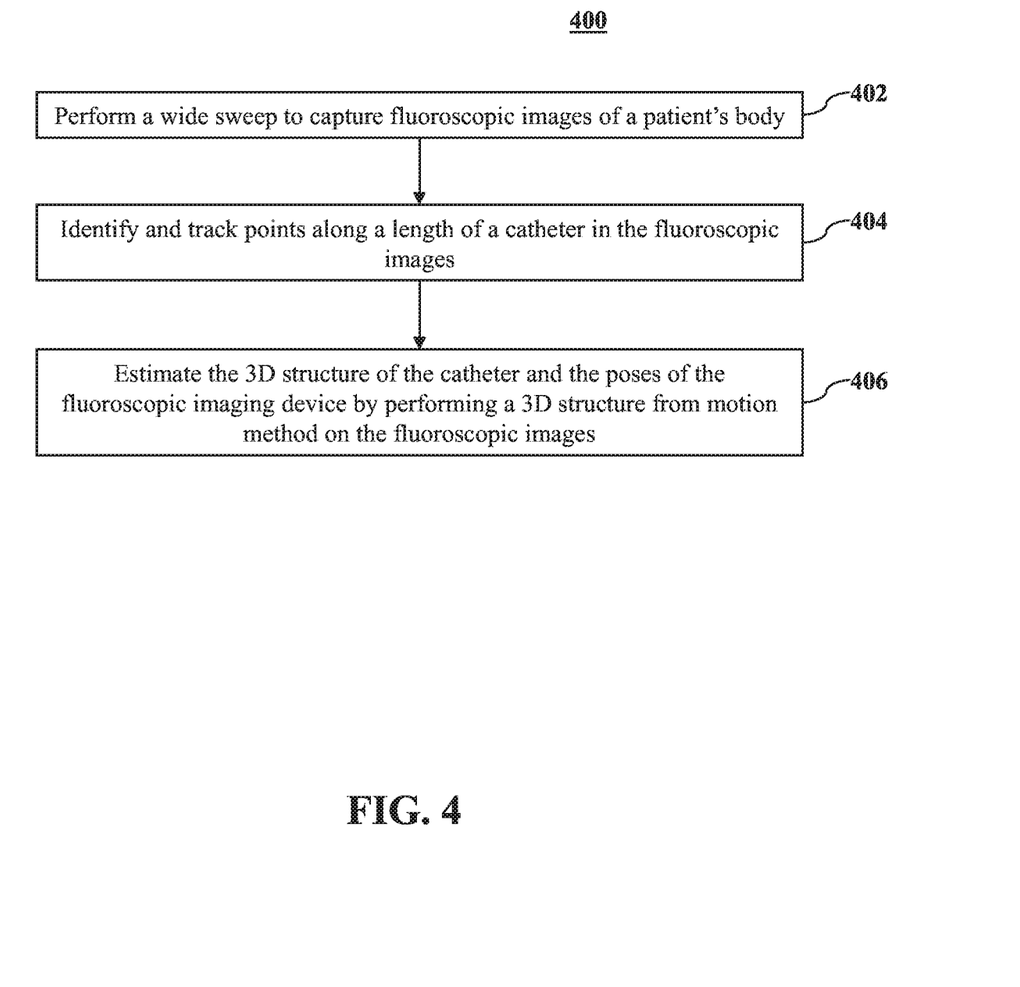
FIG. 4 is a flow chart of another method for estimating the pose of a fluoroscopic imaging device in accordance with aspects of this disclosure.

With reference to FIG. 4, a flow chart of another method 400 for estimating a pose of a fluoroscopic imaging device is provided. At block 402, a sweep is performed to capture fluoroscopic images of a patient's body. In some aspects, the sweep includes fluoroscopic imaging device viewing angles about a longitudinal axis of the patient's body of greater than 30 degrees with respect to the anteroposterior position.

At block 404, points or features along a length of a catheter in the fluoroscopic images are identified and tracked by applying suitable image processing methods to the fluoroscopic images. In some aspects, the points are radiopaque markers disposed along the length of the catheter.

At block 406, the 3D structure of the catheter and the poses of the fluoroscopic imaging device are estimated by performing a structure from motion (i.e., motion of the fluoroscopic imaging device around a structure) method on the captured fluoroscopic video images. The structure from motion method estimates the 3D structure of the catheter from the two-dimensional fluoroscopic video image sequences. The structure from motion method may include processing multiple frames of fluoroscopic video images captured at different angles so that multiple points on the catheter can be seen in the fluoroscopic video images. For example, the structure from motion method may operate on at least four frames of the fluoroscopic video images at a time. Also, at least four points along the catheter are captured in the fluoroscopic video images.

In aspects, the structure from motion method may be applied to any number of fluoroscopic images and any number of points along the length of the catheter that are suitable for accurately estimating the 3D structure of the catheter. At least four points may be sufficient for the structure from motion method to determine the 3D position of the points and the angle of the fluoroscopic imaging device looking at the points for each of the at least four fluoroscopic video frames. An interpolation algorithm may be applied to the 3D position of the points to obtain the 3D shape of the points, which, in turn, may be used to determine the 3D shape of the catheter that includes the points. In aspects, the medical device or the catheter including the points is maintained stationary while the fluoroscopic video frames are captured.

The structure from motion method may include detecting or identifying the same point across all the fluoroscopic images and differentiating that point from the other points across all the fluoroscopic images. Detecting or identifying the same points across all the fluoroscopic images may include detecting or identifying a point at the tip of the catheter and then detecting or identifying the other points by finding the order of or counting points starting from the point at the tip of the catheter. Alternatively, detecting or identifying the same points across all the fluoroscopic images may involve tracking the points from one fluoroscopic image to the next fluoroscopic image.

In some aspects, the structure from motion method may use motion signals provided by tracking sensors or coils, e.g., radiopaque coils, disposed on the catheter. The structure from motion method includes finding the correspondence between the fluoroscopic images of the catheter and the reconstruction of the 3D structure of the catheter. To find the correspondence between fluoroscopic images, features such as corner points (edges with gradients in multiple directions) may be tracked from one fluoroscopic image to the next fluoroscopic image in the sequence of captured fluoroscopic images.

In aspects, the structure from motion method may use any suitable feature detector. For example, a scale-invariant feature transform (SIFT) may be used as the feature detector. SIFT uses the maxima from a difference-of-Gaussians (DOG) pyramid as features. The first step in SIFT is finding a dominant gradient direction. Alternatively, the speeded-up robust features (SURF) may be used as the feature detector. In SURF, the DOG is replaced with a Hessian matrix-based blob detector. Also, instead of evaluating the gradient histograms, SURF computes the sums of gradient components and the sums of their absolute values.

The features detected from all the fluoroscopic images are then matched. A matching algorithm that track features from one fluoroscopic image to another fluoroscopic image is the Lukas-Kanade tracker. In some aspects, the matched features may be filtered to filter out incorrectly matched features. A random sample consensus (RANSAC) algorithm may be used to remove the incorrectly matched features.

The feature trajectories over time are then used to reconstruct their 3D positions and the fluoroscopic imaging device's motion or poses. Alternatively, the structure from motion method may use a direct approach, where geometric information (e.g., the 3D structure of the catheter and the poses of the fluoroscopic imaging device) is directly estimated from the fluoroscopic images without intermediate abstraction to features or corners.

The structure from motion method may be performed incrementally or globally. According to the incremental structure from motion approach, the poses of the fluoroscopic imaging device are solved for and added one by one to a collection. In the global structure from motion approach, the poses of the fluoroscopic imaging device are solved for at the same time. Alternatively, the structure from motion method may use an intermediate approach, where several partial reconstructions are computed and integrated into a global solution.

Figure 5A:
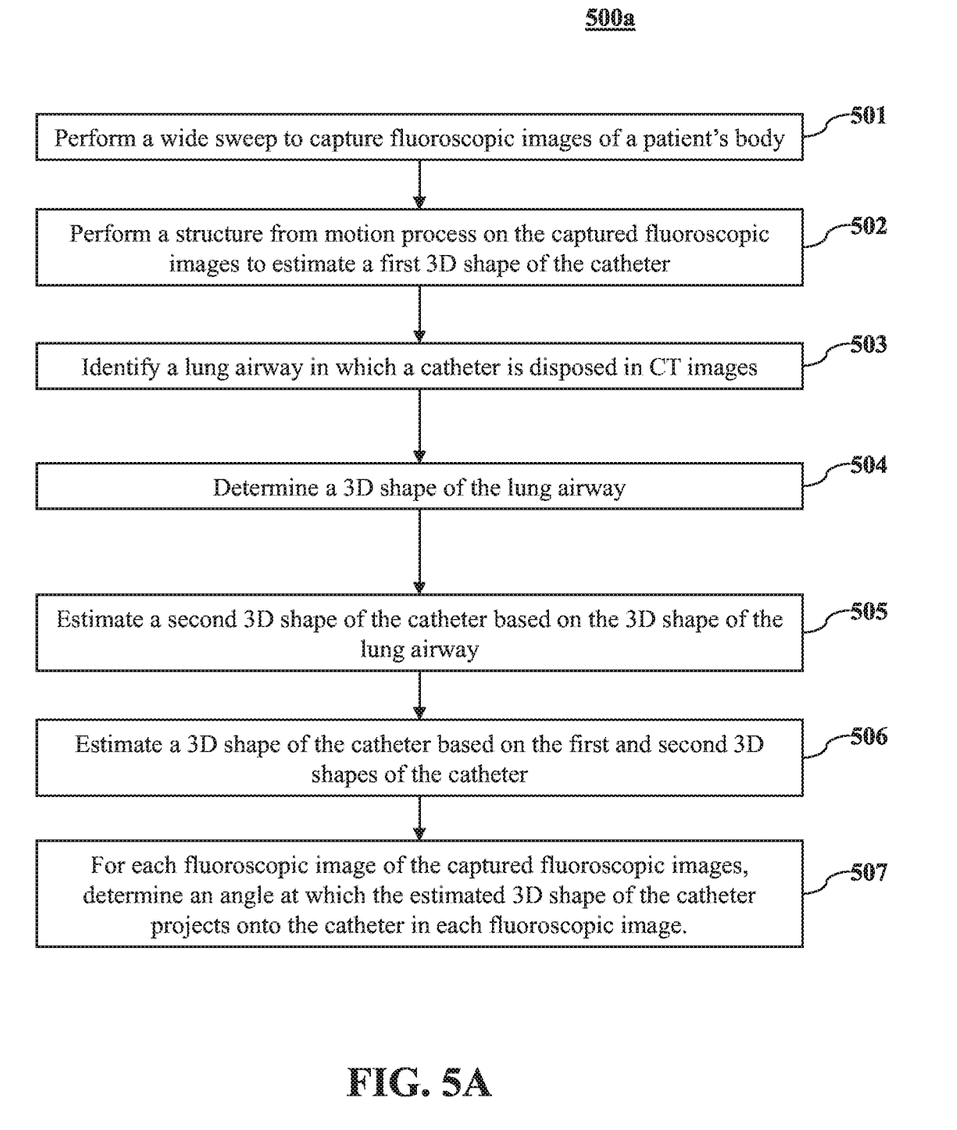
FIGS. 5A and 5B are flow charts of still other methods for estimating the pose of a fluoroscopic imaging device in accordance with aspects of this disclosure.

With reference to FIG. 5A, a flow chart of still another method 500a for estimating a pose or angle of a fluoroscopic imaging device while capturing fluoroscopic images of a patient's body is provided. At block 501, a wide fluoroscopic sweep is performed to capture fluoroscopic images of a patient's body. At block 502, a structure from motion process is performed on the first fluoroscopic images to estimate a first 3D shape of the catheter. The structure from motion process may include alternating between: (1) estimating a position of the fluoroscopic imaging device that minimizes projection error given a set of corresponding 2D and 3D coordinates of the catheter, and (2) estimating (a) 3D coordinates of the catheter given corresponding 2D coordinates of the catheter in the captured fluoroscopic images and (b) pose of the fluoroscopic imaging device.

At blocks 503-505, a second 3D shape of a catheter is determined. Specifically, a lung airway in which the catheter is disposed is identified at block 503. The lung airway in which the catheter is disposed may be identified by determining the location of the catheter (e.g., by using the electromagnetic location system and a tracking sensor or coil disposed on the catheter) with respect to preoperative computed tomography (CT) images of a lung. In other aspects, the method 500a may be applied to other body structures suitable for or capable of defining the shape of the catheter which is disposed in the other body structures. For example, the body structure may be a pathway within a lumen of a patient's body.

At block 504, a 3D shape of the lung airway is determined, for example, based on the preoperative CT images of the lung. At block 505, the second 3D shape of the catheter is estimated based on the 3D shape of the body structure. At block 506, a 3D shape of the catheter is estimated based on the first and second estimated 3D shapes of the catheter. This estimation process may include using the second estimated 3D shape to correct the first estimated 3D shape of the catheter. Then, at block 507, for each fluoroscopic image of the captured fluoroscopic images, an angle at which the estimated 3D shape of the catheter projects onto the 2D catheter in each fluoroscopic image is determined. In aspects, the determined angle may be used to reconstruct 3D volumetric data of a target area within a patient's body. Alternatively, the 3D shape of the catheter may be determined by performing a 3D shape sensing method. For example, the catheter may include one or more fiber-optic sensors, e.g., one or more spun multicore fibers, disposed along a length of the catheter, and the 3D shape of the catheter may be determined by performing a 3D shape sensing method based on fiber-optic sensor signals obtained from the one or more fiber-optic sensor With reference to FIG. 5B, a flow chart of still another method 500b for estimating a pose or angle of a fluoroscopic imaging device while capturing fluoroscopic images of a patient's body is provided. At blocks 512-514, a three-dimensional (3D) shape of a catheter is determined. Specifically, a wide sweep with the fluoroscopic imaging device is performed to capture first fluoroscopic images of the catheter and a grid of markers, e.g., spheres or other suitable markers, and second fluoroscopic images of the catheter, at block 512. Next, the pose of the fluoroscopic imaging device is estimated for each image of the first fluoroscopic images of the catheter based on a projection of the grid of markers on each image of the first fluoroscopic images of the catheter at block 513. Then, the 3D shape of the catheter is reconstructed based on the estimated poses of the fluoroscopic imaging device and the first fluoroscopic images, at block 514. The first fluoroscopic images may correspond to fluoroscopic imaging device viewing angles about a longitudinal axis of the patient of less than 30 degrees with respect to an anteroposterior position.

Figure 5B:
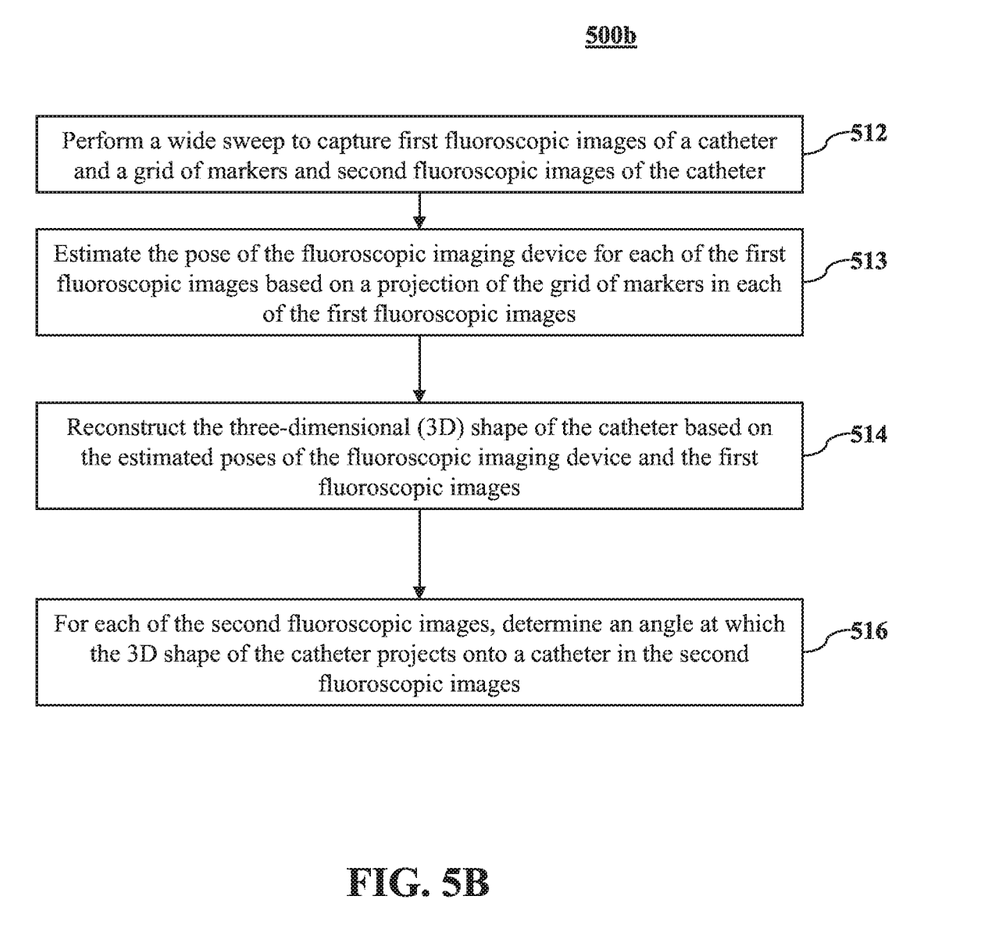

In aspects, the 3D shape of the catheter may be determined at block 514 based on poses or angles of the fluoroscopic imaging device estimated according to the following method. First, a probability map is generated for each fluoroscopic image of the first fluoroscopic images indicating the probability of each pixel of each fluoroscopic image of the first fluoroscopic images to belong to a projection of a marker of the structure or grid of markers. Next, different candidates for the projection of the structure of markers on each fluoroscopic image of the first fluoroscopic images are generated by virtually positioning the fluoroscopic imaging device in possible different possible poses. The candidates having the highest probability of being the projection of the structure of markers on each fluoroscopic image of the first fluoroscopic images are identified based on the image probability map. Then, the poses or angles of the fluoroscopic imaging device are estimated based on the virtual poses of the fluoroscopic imaging device used to generate the identified candidates.

At block 516, for each fluoroscopic image of the second fluoroscopic images, an angle at which the 3D shape of the catheter projects onto the catheter shown in the second fluoroscopic images is determined. The angles may then be used to reconstruct 3D volumetric data of a target area that includes the catheter.

Figure 6:
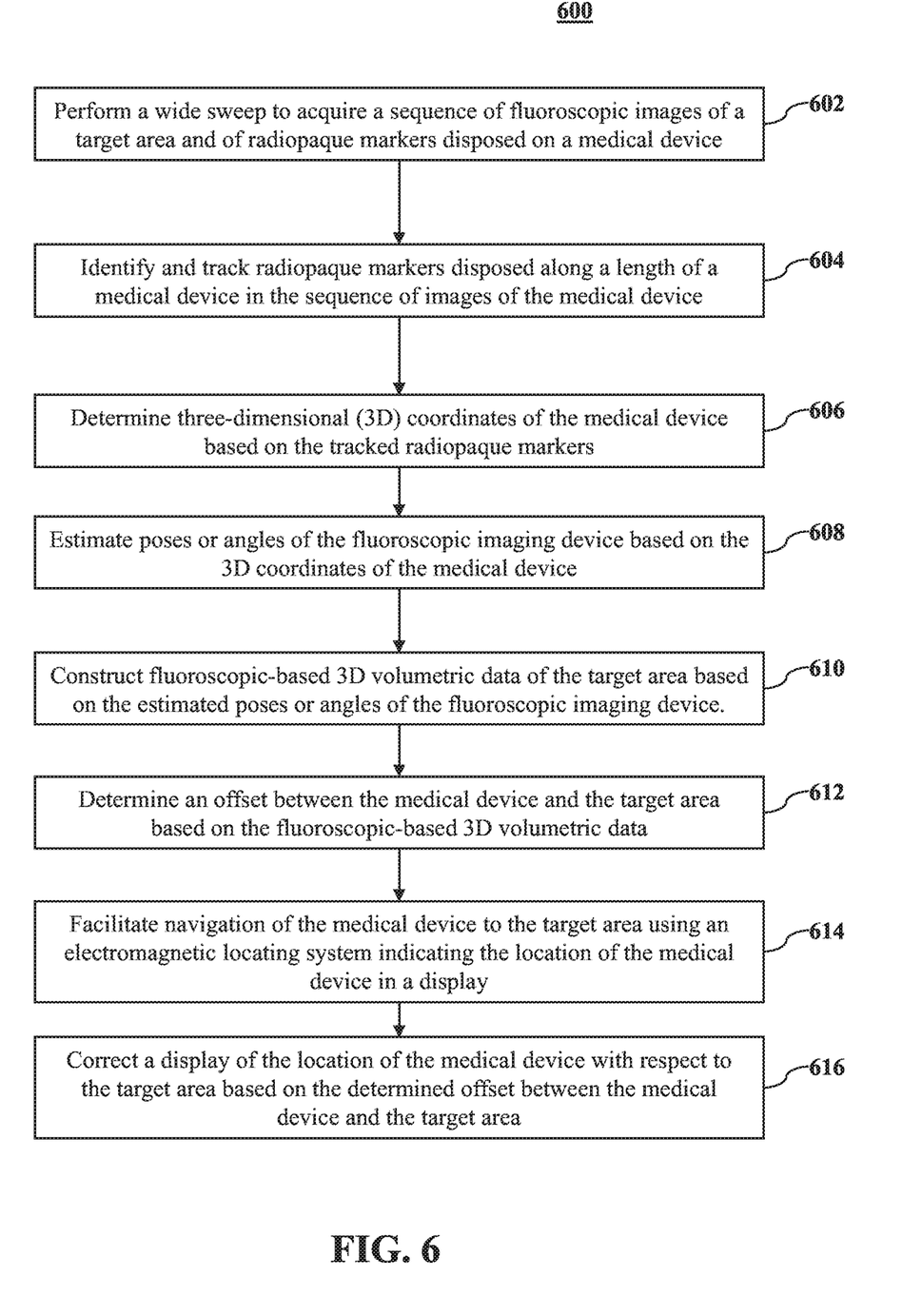
FIG. 6 is a flow chart of a method for generating 3D volumetric data in accordance with aspects of this disclosure.

With reference to FIG. 6, a flow chart of a method 600 for constructing fluoroscopic-based three-dimensional volumetric data of a target area within a patient's body is shown. At block 602, a fluoroscopic sweep is performed to acquire a sequence of fluoroscopic images of the target area and of radiopaque markers disposed on a medical device are acquired by a fluoroscopic imaging device. The target area may include at least a portion of lungs and the medical device may be navigated to the target area through an airways luminal network.

At block 604, radiopaque markers along a length of a medical device, e.g., a catheter, in the sequence of fluoroscopic images are identified and tracked using a suitable image processing algorithm. At block 606, three-dimensional (3D) coordinates of the medical device are determined based on the tracked radiopaque markers. At block 608, poses or angles of the fluoroscopic imaging device are estimated based on the 3D coordinates of the medical device. At block 610, fluoroscopic-based three-dimensional volumetric data of the target area is constructed based on the estimated poses or angles of the fluoroscopic imaging device.

In aspects, the method 600 further includes determining an offset between the medical device and the target area based on the fluoroscopic-based three-dimensional volumetric data at block 612. In further aspects, the method 600 includes facilitating navigation of the medical device to the target area using an electromagnetic locating system indicating the location of the medical device in a display at block 614, and correcting a display of the location of the medical device with respect to the target are based on the determined offset between the medical device and the target area at block 616.

In still further aspects, the method may include displaying a 3D rendering of the target area on the display and registering the electromagnetic locating system to the 3D rendering. The correcting of the location of the medical device with respect to the target may include updating registration of the electromagnetic locating system to the 3D rendering.

In aspects, the method may include generating the 3D rendering of the target area based on previously-acquired CT volumetric data of the target area. The target area may include at least a portion of lungs, a soft-tissue target area, or an ablation target.

From the foregoing and with reference to the various figure drawings, those skilled in the art will appreciate that certain modifications can also be made to this disclosure without departing from the scope of the same. For example, although the systems and methods are described as usable with an EMN system for navigation through a luminal network such as the lungs, the systems and methods described herein may be utilized with systems that utilize other navigation and treatment devices such as percutaneous devices. Additionally, although the above-described system and method is described as used within a patient's luminal network, it is appreciated that the above-described systems and methods may be utilized in other target regions such as the liver. Further, the above-described systems and methods are also usable for transthoracic needle aspiration procedures.

Detailed aspects are disclosed herein. However, the disclosed aspects are merely examples of the disclosure, which may be embodied in various forms and aspects. Therefore, specific structural and functional details disclosed herein are not to be interpreted as limiting, but merely as a basis for the claims and as a representative basis for teaching one skilled in the art to variously employ this disclosure in virtually any appropriately detailed structure.

As can be appreciated a medical instrument such as a biopsy tool or an energy device, such as a microwave ablation catheter, that is positionable through one or more branched luminal networks of a patient to treat tissue may prove useful in the surgical arena and this disclosure is directed to systems and methods that are usable with such instruments and tools. Access to luminal networks may be percutaneous or through a natural orifice using navigation techniques. Additionally, navigation through a luminal network may be accomplished using image-guidance systems. The image-guidance systems may be separate or integrated with the energy device or a separate access tool and may include MRI, CT, fluoroscopy, ultrasound, electrical impedance tomography, optical, and/or device tracking systems.

Methodologies for locating the access tool include EM, IR, echolocation, optical, and others. Tracking systems may be integrated to an imaging device, where tracking is done in virtual space or fused with preoperative or live images. In some cases, the treatment target may be directly accessed from within the lumen, such as for the treatment of the endobronchial wall for COPD, Asthma, lung cancer, etc. In other cases, the energy device and/or an additional access tool may be required to pierce the lumen and extend into other tissues to reach the target, such as for the treatment of disease within the parenchyma. Final localization and confirmation of energy device or tool placement may be performed with imaging and/or navigational guidance using a standard fluoroscopic imaging device incorporated with methods and systems described above.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope and spirit of the claims appended hereto.

What is claimed is:

1. A method comprising:
   receiving a plurality of fluoroscopic images of movement of a catheter captured by a fluoroscopic imaging device;
   identifying a plurality of radiopaque tracking sensors along a length of the catheter in the plurality of fluoroscopic images of the movement of the catheter, yielding an identified plurality of radiopaque tracking sensors;
   tracking, in the plurality of fluoroscopic images, movement of the identified plurality of radiopaque tracking sensors, yielding a tracked movement of the plurality of radiopaque tracking sensors;
   determining three-dimensional (3D) coordinates of the catheter by performing a 3D structure from motion method on the tracked movement of the plurality of radiopaque tracking sensors;
   determining a 3D shape of a body structure in which the catheter is disposed;
   estimating poses of the fluoroscopic imaging device based on the 3D coordinates of the catheter and the 3D shape of the body structure;
   determining, by an electromagnetic (EM) locating system, a location of the catheter based on signals from the plurality of radiopaque tracking sensors, yielding a determined location of the catheter; and
   facilitating navigation of the catheter to a target area by indicating the determined location of the catheter in a display.

2. The method of claim 1, wherein the plurality of radiopaque tracking sensors is a plurality of radiopaque coils.

3. The method of claim 1, wherein a sweep of the fluoroscopic imaging device to capture the plurality of fluoroscopic images is a wide sweep including fluoroscopic imaging device viewing angles about a longitudinal axis of greater than 30 degrees with respect to an anteroposterior position.

4. A method comprising:
   receiving a sequence of a plurality of fluoroscopic images of a patient's body captured by a fluoroscopic imaging device;
   identifying a plurality of radiopaque markers along a length of a catheter in the sequence of the plurality of fluoroscopic images of the catheter advancing through a patient's body, yielding an identified plurality of radiopaque markers;
   tracking the identified plurality of radiopaque markers, yielding tracked movement of the plurality of radiopaque markers;
   performing a 3D structure from motion method on the tracked movement of the plurality of radiopaque markers to estimate a first three-dimensional (3D) shape of the catheter;
   determining a 3D shape of a body structure in which the catheter is disposed;
   estimating a second 3D shape of the catheter based on the 3D shape of the body structure in which the catheter is disposed;
   estimating a third 3D shape of the catheter based on the first 3D shape and the second 3D shape; and
   estimating poses of the fluoroscopic imaging device based on the third 3D shape of the catheter.

5. The method of claim 4, further comprising constructing 3D volumetric data of an area based on the poses of the fluoroscopic imaging device.

6. The method of claim 4, wherein a sweep of the fluoroscopic imaging device to capture the plurality of fluoroscopic images is a wide sweep including fluoroscopic imaging device viewing angles about a longitudinal axis of the patient's body greater than 50 degrees with respect to an anteroposterior position.

7. The method of claim 4, wherein the 3D shape of the body structure in which the catheter is disposed is determined based on computed tomography (CT) images of the body structure in which the catheter is disposed.

8. The method of claim 4, wherein the body structure is an airway of a lung.

9. A method for constructing fluoroscopic-based three-dimensional volumetric data of a target area within a patient's body, comprising:
   acquiring a sequence of fluoroscopic images of the target area and movement of a plurality of radiopaque locating sensors of a medical device;
   identifying the plurality of radiopaque locating sensors along a length of the medical device in the sequence of fluoroscopic images of the medical device advancing through a patient's body, yielding an identified plurality of radiopaque locating sensors;
   tracking, in the sequence of fluoroscopic images, movement of the identified plurality of radiopaque locating sensors, yielding a tracked movement of the plurality of radiopaque locating sensors;
   determining three-dimensional (3D) coordinates of the medical device by performing a 3D structure from motion method on the tracked movement of the plurality of radiopaque locating sensors;
   determining a 3D shape of a body structure in which the medical device is disposed;
   estimating angles of a fluoroscopic imaging device based on the 3D coordinates of the medical device and the 3D shape of the body structure;
   constructing fluoroscopic-based 3D volumetric data of the target area based on the angles of the fluoroscopic imaging device;
   determining, by an electromagnetic (EM) locating system, a location of the medical device based on signals from the plurality of radiopaque locating sensors, yielding a determined location of the medical device; and
   indicating the determined location of the medical device in a display.

10. The method of claim 9, further comprising determining an offset between the medical device and the target area based on the fluoroscopic-based 3D volumetric data.

11. The method of claim 10, further comprising correcting a display of the determined location of the medical device with respect to the target area based on the offset between the medical device and the target area.

12. The method of claim 11, further comprising:
    displaying a 3D rendering of the target area on the display; and
    registering the EM locating system to the 3D rendering,
    wherein the correcting of the determined location of the medical device with respect to the target area comprises updating registration of the EM locating system to the 3D rendering.

13. The method of claim 12, further comprising generating the 3D rendering of the target area based on previously-acquired CT volumetric data of the target area.

14. The method of claim 9, wherein the target area comprises at least a portion of a lung, and
    wherein the medical device is navigated to the target area through an airway of a luminal network of the lung.

15. The method of claim 9, wherein the target area comprises at least a portion of a lung.

16. The method of claim 9, wherein the target area includes a soft-tissue target.

17. The method of claim 9, wherein the target area includes a target to be ablated.

* * * * *